United States Patent [19]

Evers et al.

[11] Patent Number: 4,560,802

[45] Date of Patent: Dec. 24, 1985

[54] SYNTHESIS OF TRICONJUGATED DIENONES AND NOVEL INTERMEDIATES USED IN SAID PROCESS

[75] Inventors: William J. Evers, Locust; Gilbert Stork, Englewood; Braja D. Mookherjee, Holmdel; Howard H. Heinsohn, Jr., Freehold, all of N.J.

[73] Assignee: International Flavors & Fragrances Inc., New York, N.Y.

[21] Appl. No.: 620,086

[22] Filed: Jun. 13, 1984

Related U.S. Application Data

[62] Division of Ser. No. 551,480, Nov. 14, 1983, which is a division of Ser. No. 431,268, Sep. 30, 1982, Pat. No. 4,451,392.

[51] Int. Cl.⁴ .............................................. C07C 45/65
[52] U.S. Cl. .................... 568/388; 560/266; 560/262
[58] Field of Search .............. 568/298, 407, 393, 388; 560/262, 266

[56] References Cited

U.S. PATENT DOCUMENTS

| | | | |
|---|---|---|---|
| 1,737,203 | 11/1929 | Scholler et al. | 568/407 |
| 2,006,198 | 6/1935 | Frolich et al. | 568/407 |
| 2,194,704 | 3/1940 | Kroeger | 568/407 |
| 4,346,237 | 8/1982 | Boden | 568/407 |

OTHER PUBLICATIONS

Adams et al, J. Chem. Soc., Perkin I, 1975, pp. 1741–1743.
Thomas, Anhydrous Aluminum Chloride in Organic Chemistry, pp. 752–757, (1941).
Young, "Protective Groups in Organic Chemistry", pp. 309–321, (1973).
Fieser et al, Reagents for Organic Synthesis, vol. 4, pp. 414–415, (1978).

*Primary Examiner*—James H. Reamer
*Attorney, Agent, or Firm*—Arthur L. Liberman

[57] ABSTRACT

Described is a process for preparing triconjugated dienones defined according to the structure:

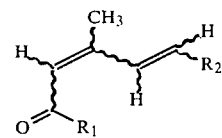

wherein $R_1$ represents $C_1$–$C_8$ alkyl, phenyl or phenyl methyl and wherein $R_2$ represents hydrogen or $C_1$–$C_5$ lower alkyl; and wherein the wavy lines are indicative of a "cis" or a "trans" juxtaposition of the $R_2$, methyl, acyl or vinyl moieties about one or both of the carbon-carbon double bonds which process involves the reaction of an acyl halide having the structure:

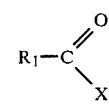

(wherein X represents chloro)
with a substituted or unsubstituted prenyl ester having the structure:

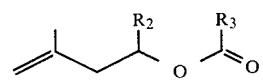

wherein $R_3$ represents $C_1$–$C_5$ alkyl in the presence of an aluminum chloride catalyst and a methylene dichloride solvent in order to form the novel intermediate genus defined according to the structure:

(Abstract continued on next page.)

then dehydrohalogenating the compound defined according to the structure:

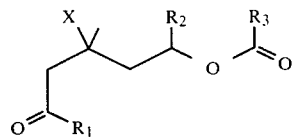

using an alkali metal carbonate and a dimethylformamide solvent in order to form the novel compound genus having the structure:

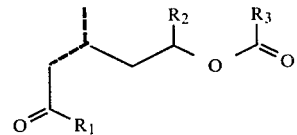

wherein one of the dashed lines represents a carbon-carbon double bond and the other of the dashed lines represents a carbon-carbon single bond; and then dehydrocyloxylating the compound having the structure:

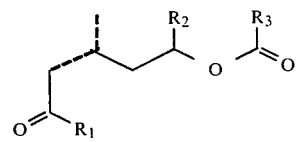

in order to form the compound having the structure:

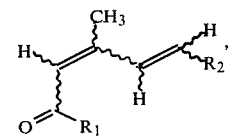

the dehydroacyloxylation step taking place in the presence of an alkali metal carbonate and dimethylformamide solvent.

2 Claims, 10 Drawing Figures

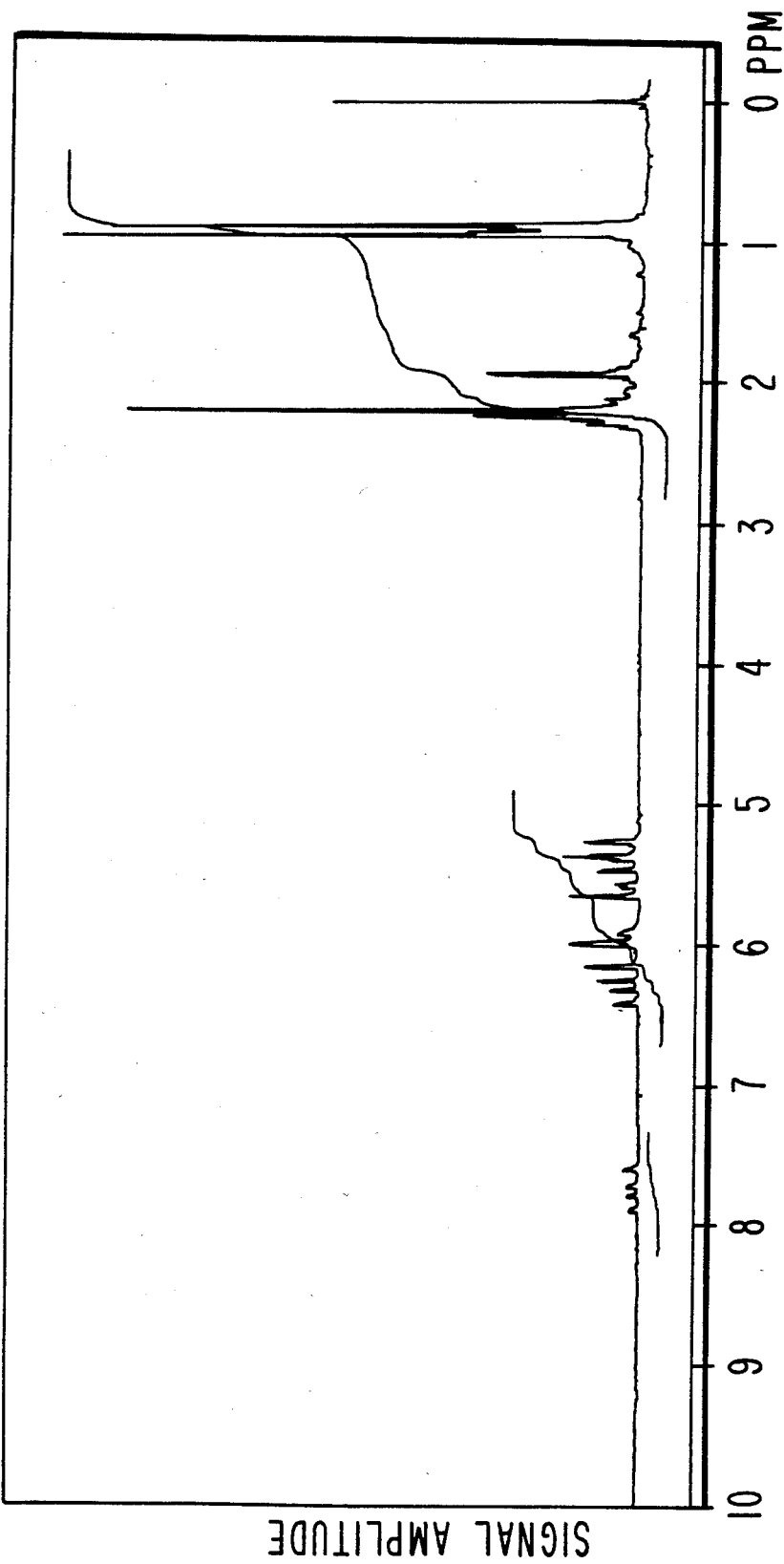
FIG.1 NMR SPECTRUM FOR EXAMPLE II.

GLC PROFILE FOR EXAMPLE IV.

GLC PROFILE FOR EXAMPLE III.

GLC PROFILE FOR EXAMPLE V.

GLC PROFILE FOR EXAMPLE XI(B).

GLC PROFILE FOR EXAMPLE VII B.

IR SPECTRUM FOR EXAMPLE VII B.

SYNTHESIS OF TRICONJUGATED DIENONES AND NOVEL INTERMEDIATES USED IN SAID PROCESS

This is a division of application Ser. No. 551,480, filed Nov. 14, 1983, which, in turn, is a division of application Ser. No. 431,268, filed Sept. 30, 1982, now U.S. Pat. No. 4,451,392 issued May 29, 1984.

BACKGROUND OF THE INVENTION

The instant invention relates to a new synthesis which for the first time makes it commercially feasible to synthesize triconjugated dienones defined according to the structure:

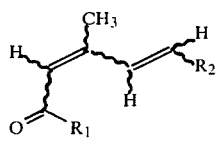

wherein $R_1$ represents $C_1$–$C_8$ alkyl, phenyl or phenyl methyl and wherein $R_2$ represents hydrogen or $C_1$–$C_5$ lower alkyl; and wherein the wavy lines are indicative of a "cis" or "trans" juxtaposition of the $R_2$, methyl, acyl or vinyl moieties about one or both of the carbon-carbon double bonds which process involves the reaction of an acyl halide having the structure:

(wherein X represents chloro)
with a substituted or unsubstituted prenyl ester having the structure:

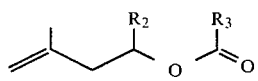

wherein $R_3$ represents $C_1$–$C_5$ alkyl in the presence of an aluminum chloride catalyst and a methylene dichloride solvent in order to form the novel intermediate genus defined according to the structure:

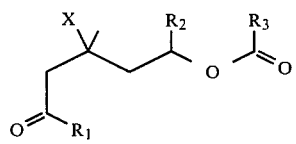

then dehydrohalogenating the compound defined according to the structure:

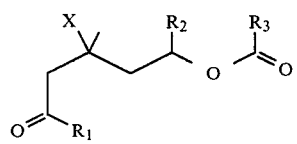

using an alkali metal carbonate and a dimethylformamide solvent in order to form the novel compound genus having the structure:

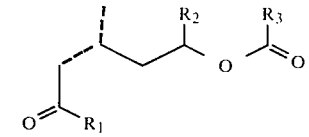

wherein one of the dashed lines represents a carbon-carbon double bond and the other of the dashed lines represents a carbon-carbon single bond; and then dehydroacyloxylating the compound having the structure:

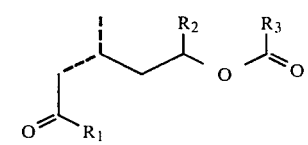

in order to form the compound having the structure:

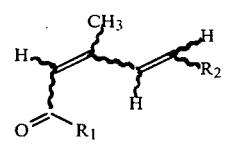

the dehydroacyloxylation step taking place in the presence of an alkali metal carbonate and dimethylformamide solvent; including mixtures of "cis" and "trans" tagetone defined according to the structure:

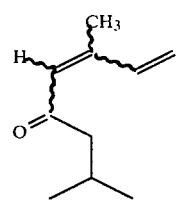

as well as "cis" and/or "trans" isomers of the compounds having the structures:

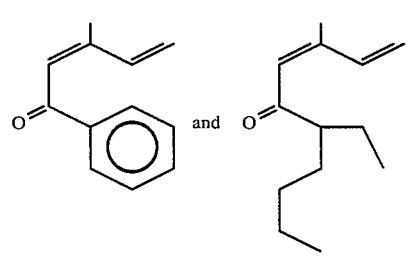

which mixtures are useful in perfumery.

Arctander "Perfume & Flavor Materials of Natural Origin, (1960), at columns 606 and 607, indicates the usefulness of Tagete oil and further indicates that "there is no suitable substitute for crude Tagete oil . . . and once these materials are established in perfume formulas the oil must be precured somehow . . . the main constituent, Tagetone, and an unstable ketone is presumably responsible for the peculiar odor and for the resinification and unstability of the oil . . . ".

Nevertheless, if tagetone is synthesized in substantially pure form via the process of the instant invention a stable useful Tagete oil substitute can be created.

Tagetone has however been previously synthesized, but these prior syntheses are highly expensive and very difficult to carry out in view of the extreme conditions required.

Thus, Adams, et al, "Journal of The Chemical Society" Perkin I, (1975), pages 1741-43, indicates the synthesis of Tagetone by means of reaction of isoprene with isovaleryl chloride in the presence of a stanic chloride (Lewis Acid) catalyst at −78° C. to form a halide which is subsequently dehydro halogenated using lithium fluoride and lithium carbonate in a dimethylformamide solvent according to the reaction sequence:

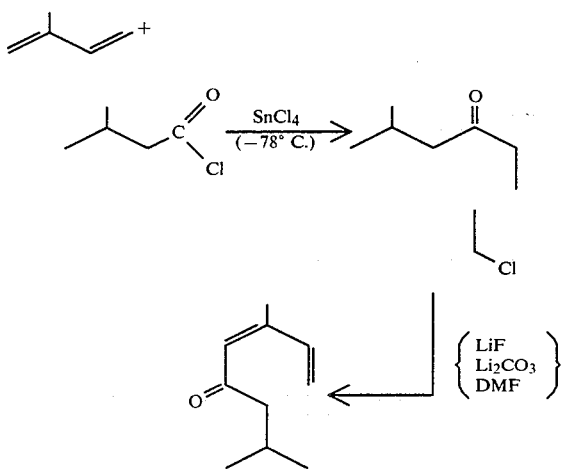

Also carried out at −78° C. is the reaction between isovaleryl chloride and a trimethyl silane complex of isoprene in a presence of a titanium tetrachloride catalyst in a methylene dichloride solvent according to the reaction:

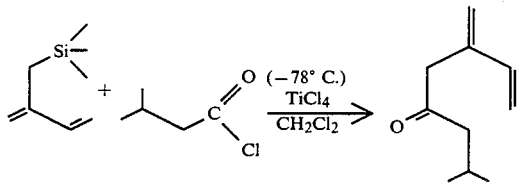

as disclosed by Hosomi, et al, Tetrahedron Letters No. 5, pages 429-32 (1979).

Garbers and Scott Tetrahedron Letters No. 19, pages 1625-1628, (1976), also discloses the production of "cis" and "trans" ocimenones which are also major constituents of oil of Tagete according to the reaction:

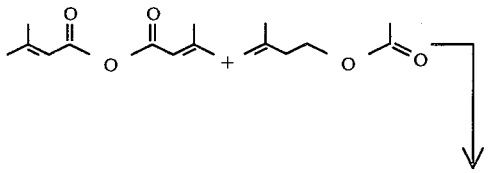

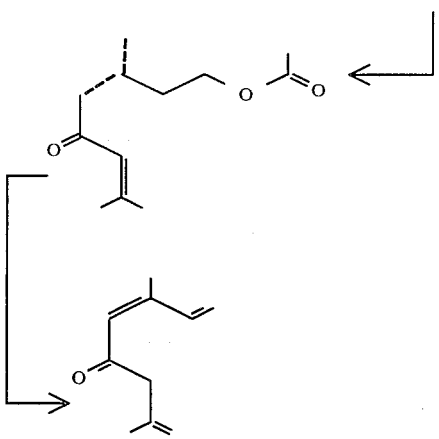

The compounds having the structures:

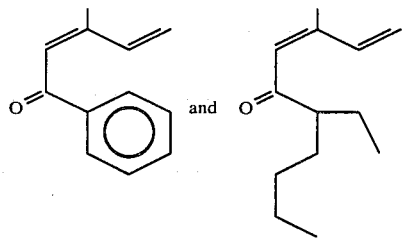

are novel compounds.

There has been considerable work performed relating to substances which can be used to impart (modify, augment or enhance) flavors and fragrances to (or in) various consumable materials. These substances are used to dimenish the use of natural materials some of which may be in short supply and to provide more uniform properties in the finished product.

Tagete-like and floral aromas are particularly desirable in several types of perfume compositions, perfumed articles (e.g., anionic, cationic, nonionic or zwitterionic detergents, fabric softener articles, perfume polymers and cosmetic powders) and colognes.

Tagete and floral aromas and tastes are desirable in connection with augmenting or enhancing the flavors or aromas of smoking tobaccos both prior to smoking and on smoking in both the main stream and the side stream.

BRIEF DESCRIPTION OF THE DRAWINGS

FIG. 1 is the NMR spectrum for tagetone produced according to Example II (E:Z ratio=10:4). Said Tagete Tagetones are shown according to the formula:

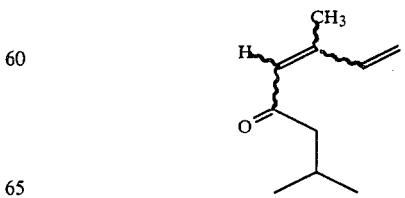

wherein the wavy lines represent "cis" and "trans" juxtaposition of the acyl, methyl and vinyl groups about the carbon-carbon double bond alpha to the acyl group (solvent: CFCl₃; field strength 100 MHz).

Figure 2:
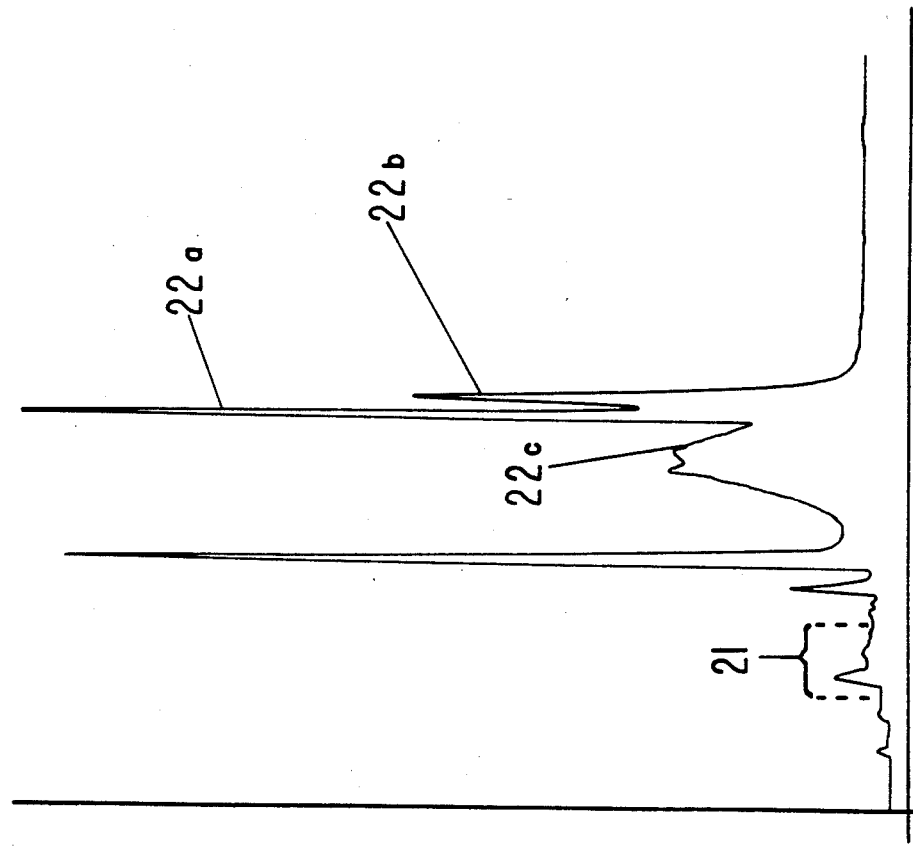

FIG. 2 is the GLC profile for the reaction product of Example III containing the compound having the structure:

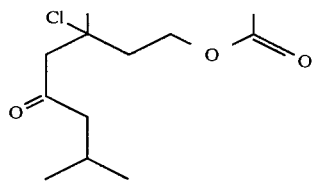

Figure 3:
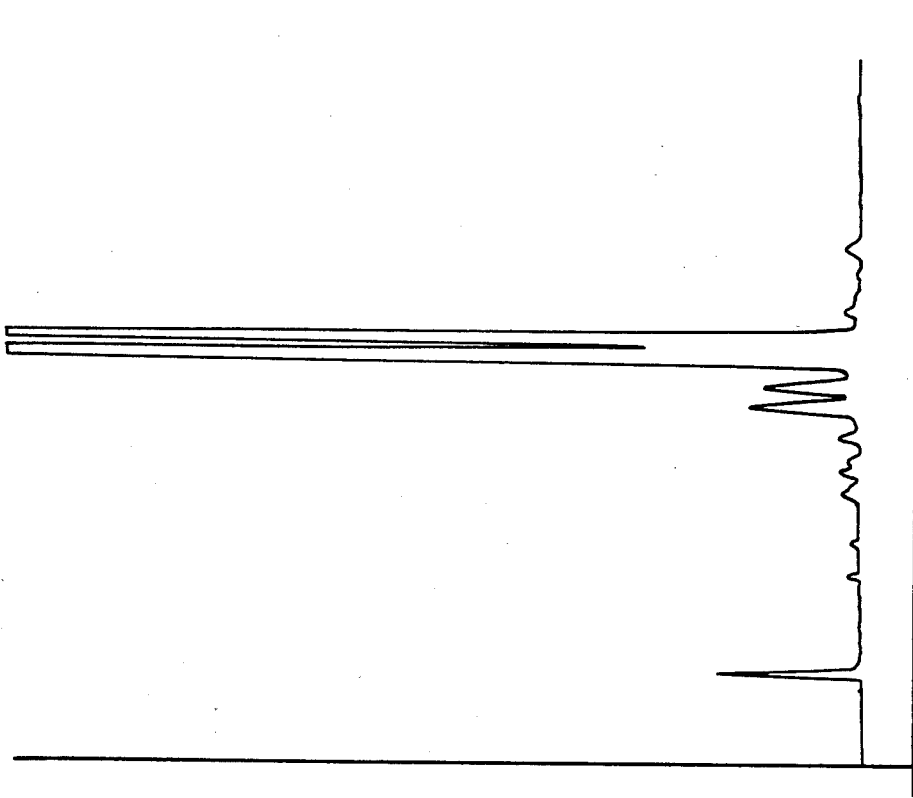

FIG. 3 is the GLC profile for the reaction product of Example IV containing the compounds defined according to the structure:

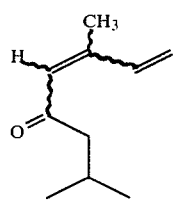

wherein the wavy lines represent the "cis" and "trans" juxtaposition of the vinyl, methyl and acyl groups around the carbon-carbon double bond which is alpha to the acyl moiety.

Figure 4:
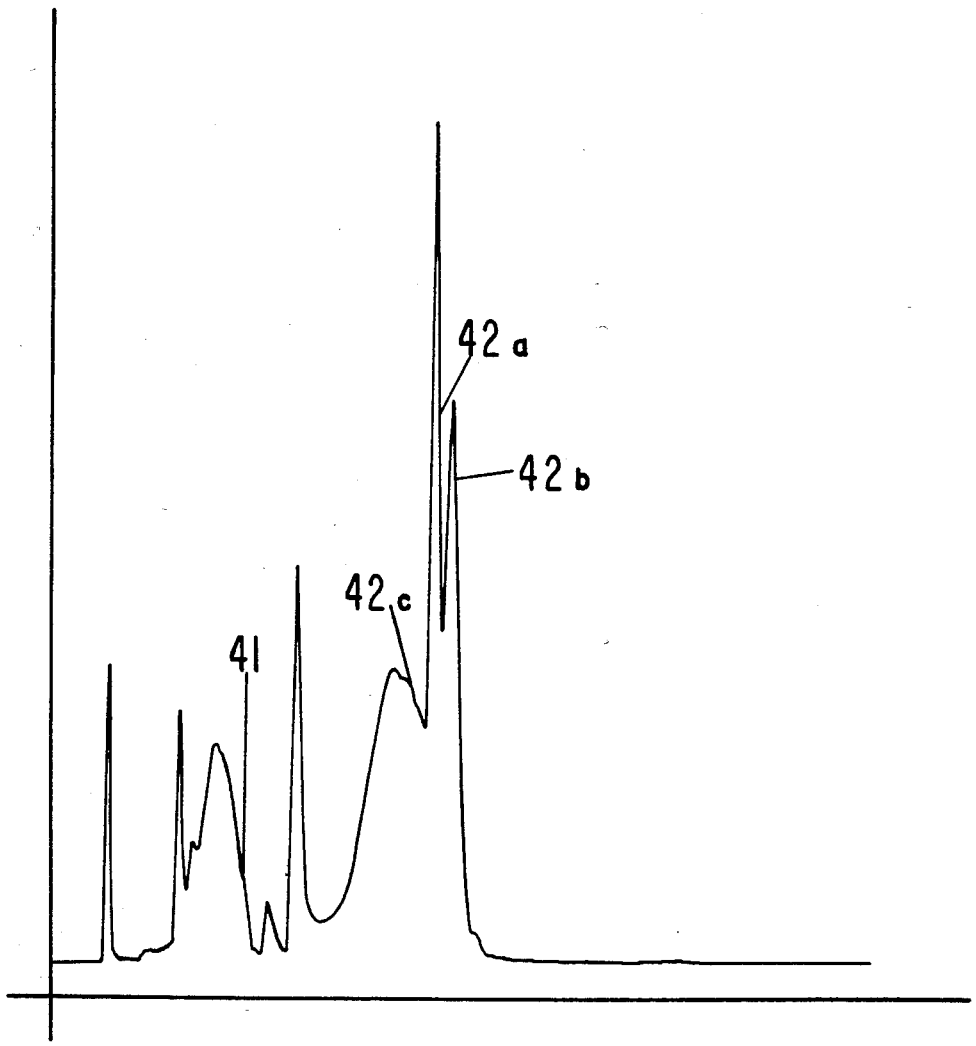

FIG. 4 is the GLC profile for the reaction product of Example V containing the compound having the structure:

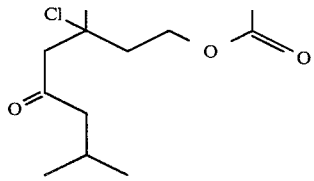

and in addition, major impurities.

Figure 5:
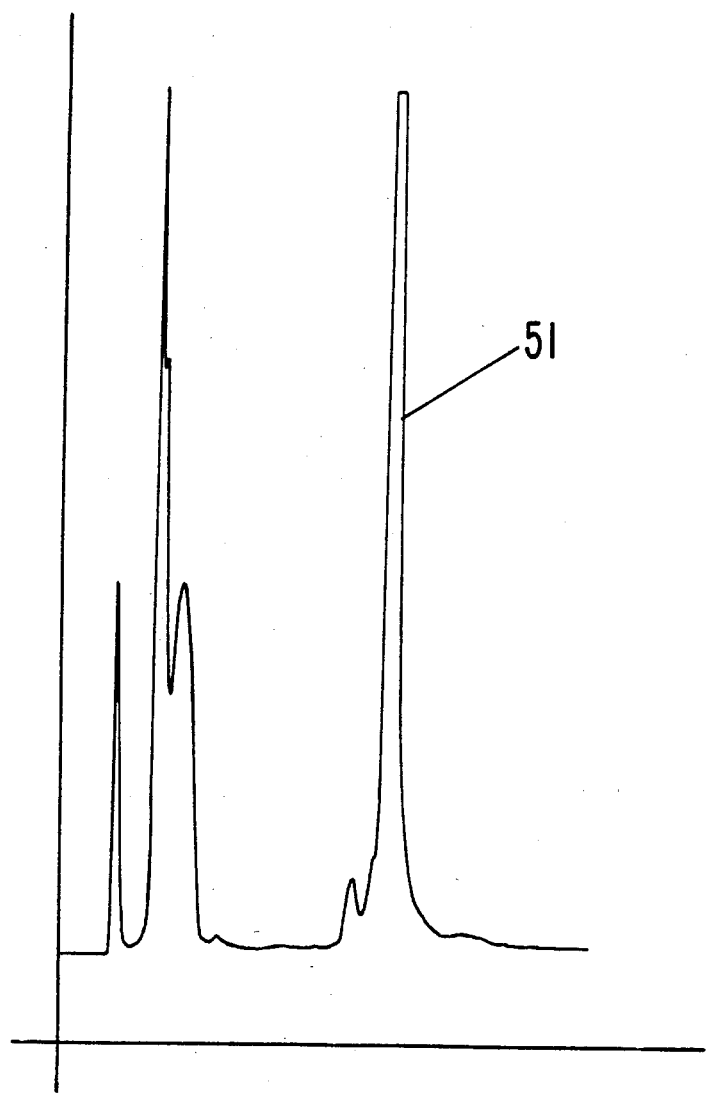

FIG. 5 is the GLC profile for the reaction product of Example IV(B) containing the compound having the structure:

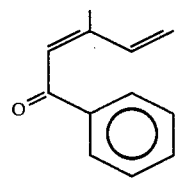

Figure 6:
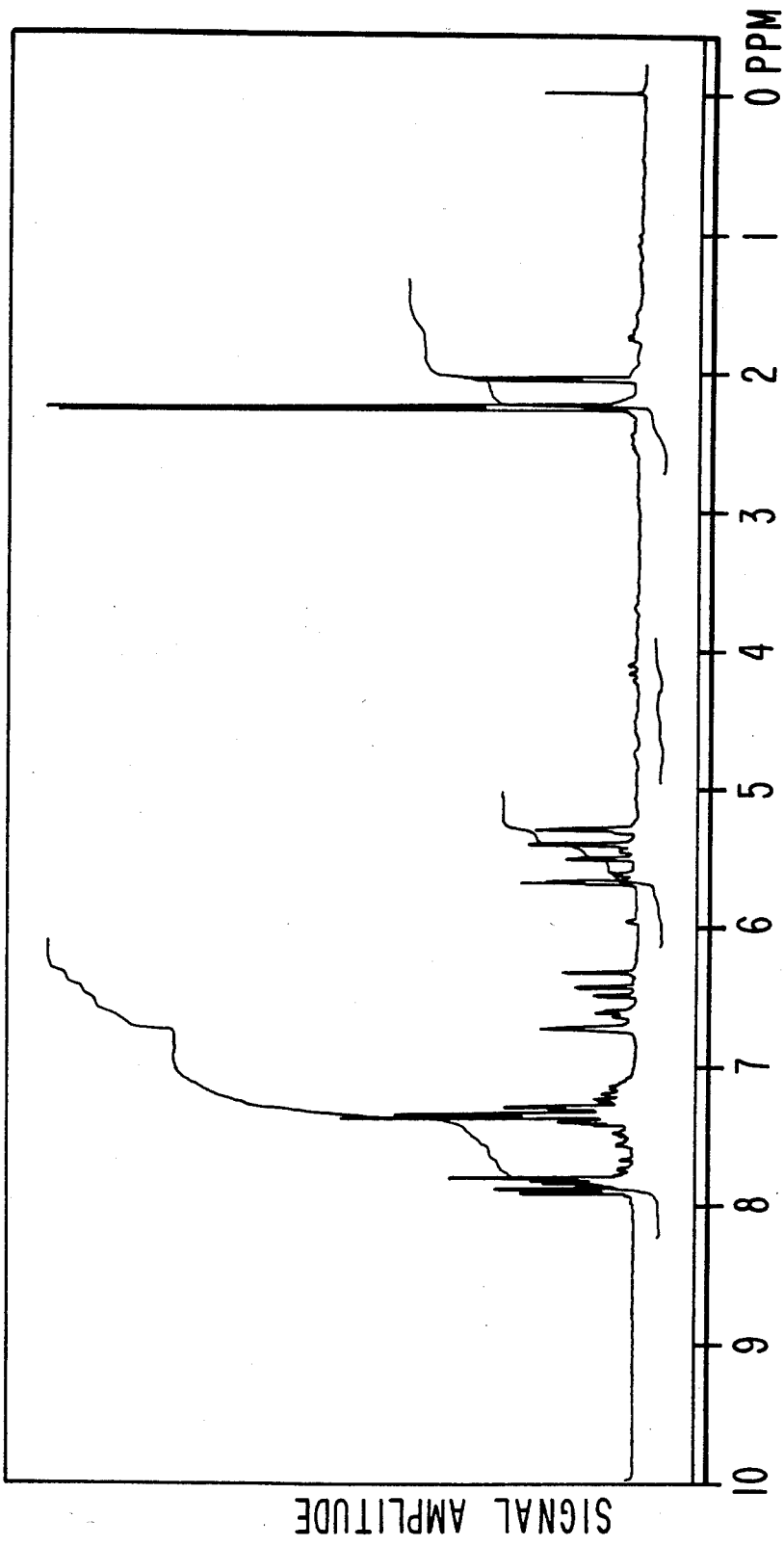

FIG. 6 is the NMR spectrum for the compound having the structure:

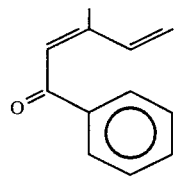

synthesized according to Example IV(B). (Solvent: CFCl₃; field strength 100 MHz).

Figure 7:
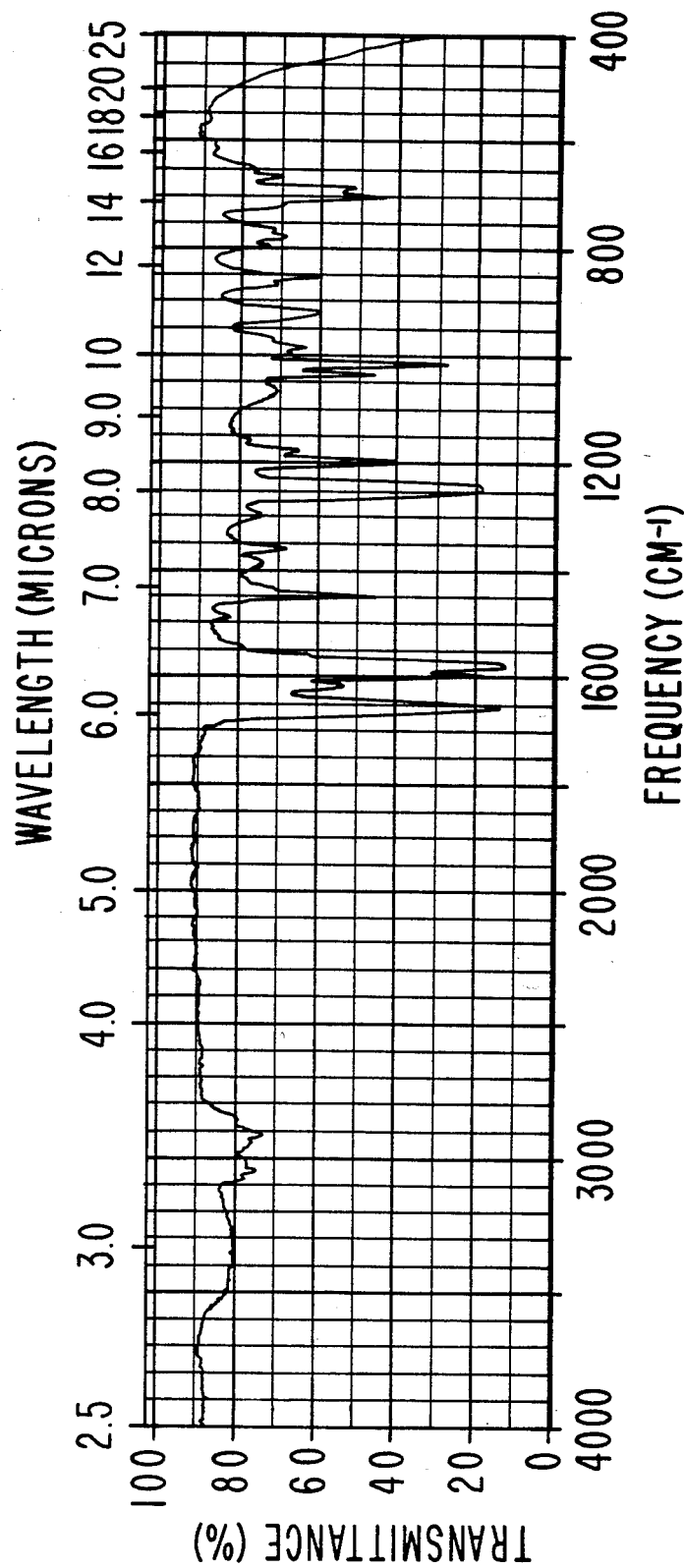

FIG. 7 is the infra-red spectrum for the compound having the structure:

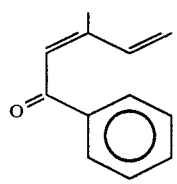

prepared according to Example IV(B).

Figure 8:
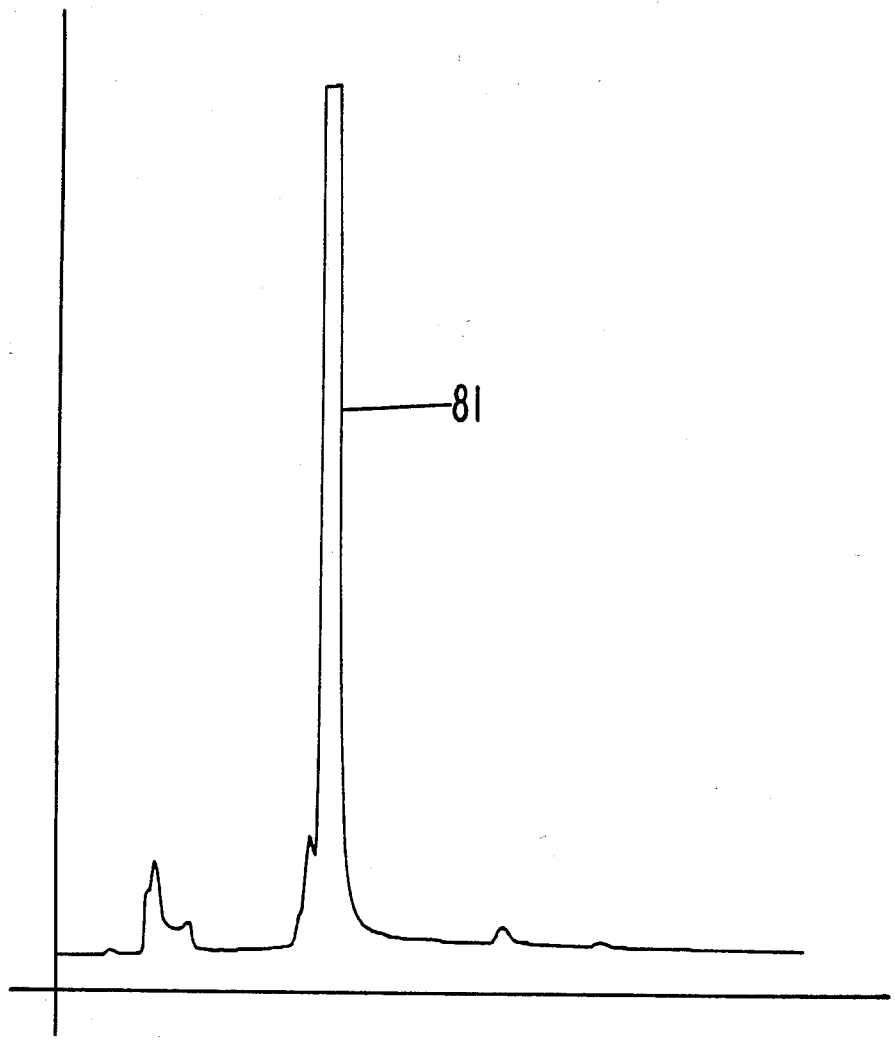

FIG. 8 is the GLC profile for the reaction product of Example VII(B) containing the compound having the structure:

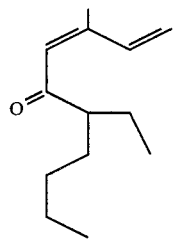

Figure 9:
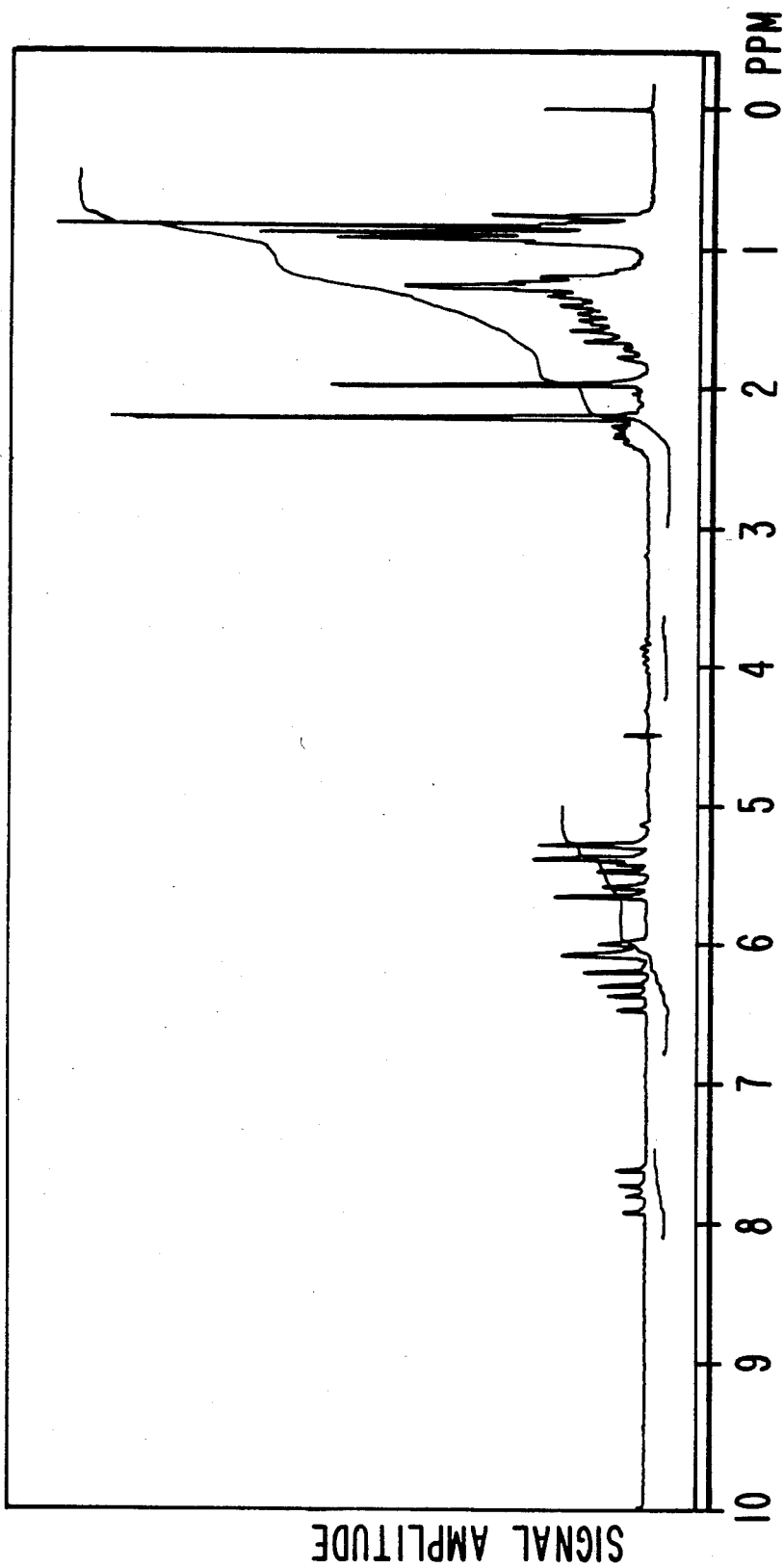

FIG. 9 is the NMR spectrum for the compound having the structure:

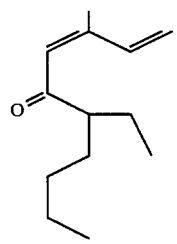

prepared according to Example VII(B). (Solvent: CFCl₃; field strength 100 MHz).

Figure 10:
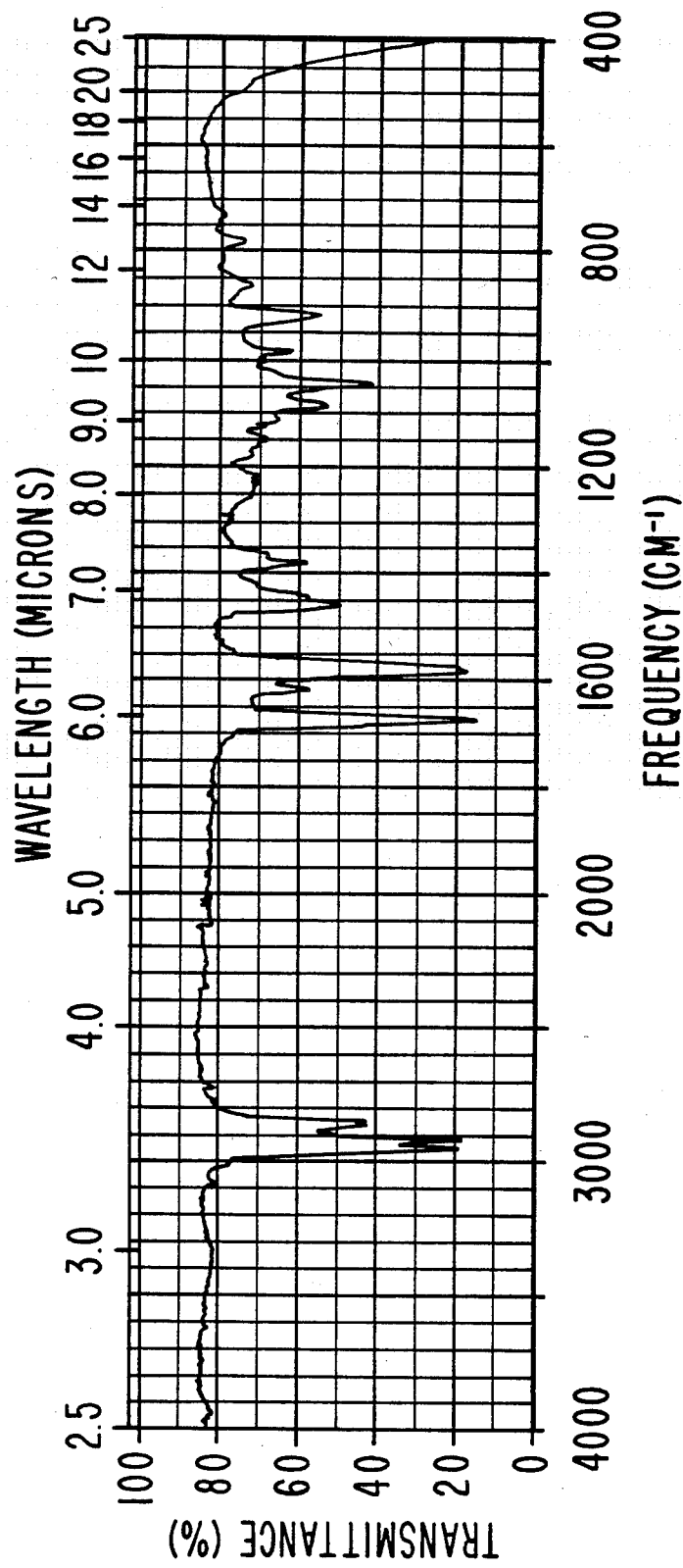

FIG. 10 is the infra-red spectrum for the compound having the structure:

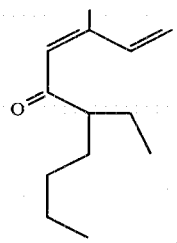

prepared according to Example VII(B).

DETAILED DESCRIPTION OF THE DRAWINGS

FIG. 2 is the GLC profile for the reaction product of Example III containing the compound having the structure:

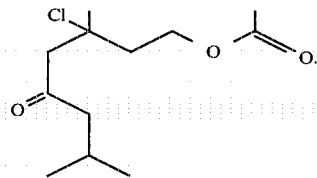

This compound is indicated at peaks 22A, 22B and 22C. The peaks indicated by reference numeral "21" are for a very minor amount of impurity in the reaction product.

Such an impurity is a major constituent in the reaction product of Example V.

FIG. 4 is the GLC profile for the reaction product of Example V containing the compound defined according to the structure:

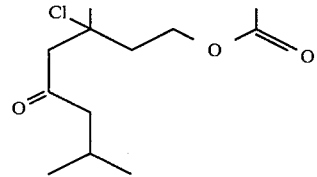

is at peaks indicated by reference numeral "42A", "42B", and "42C". The peak indicated by reference numeral "41" is the peak showing major impurities when using the Lewis acid catalyst, titanium tetrachloride instead of the Lewis acid catalyst, aluminum trichloride.

FIG. 5 is the GLC profile for the reaction product of Example VI(B). The peak indicated by reference numeral "51" is the peak for the compound having the structure:

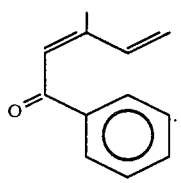

FIG. 8 is the GLC profile for the reaction product of Example VII(B). The peak indicated by reference numeral "81" is the peak for the compound having the structure:

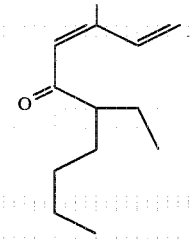

THE INVENTION

Our invention defines a commercial process for producing triconjugated dienones defined according to the generic structure:

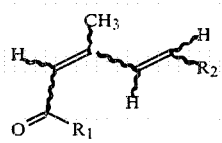

wherein $R_1$ represents $C_1$-$C_8$ alkyl, phenyl or phenyl methyl and wherein $R_2$ represents hydrogen or $C_1$-$C_5$ lower alkyl; and wherein the wavy lines are indicative of a "cis" or "trans" juxtaposition of the $R_2$, methyl, acyl or vinyl moieties about one or both of the carbon-carbon double bonds which process involves the reaction of an acyl halide having the structure:

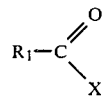

(wherein X is chloro)

with a substituted or unsubstituted prenyl ester having the structure:

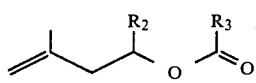

wherein $R_3$ represents $C_1$-$C_5$ alkyl in the presence of an aluminum chloride catalyst and a methylene dichloride solvent in order to form the novel intermediate genus defined according to the structure:

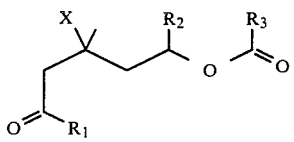

then dehydrohalogenating the compound defined according to the structure:

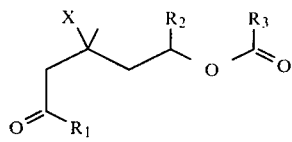

using an alkali metal carbonate and a dimethylformamide solvent in order to form the novel compound genus having the structure:

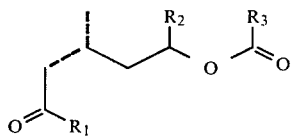

wherein one of the dashed lines represents a carbon-carbon double bond and the other of the dashed lines represents a carbon-carbon single bond; and then dehydroacyloxylating the compound having the structure:

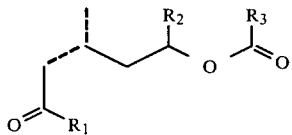

in order to form the compound having the structure:

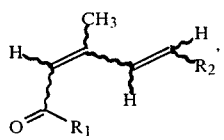

the dehydroacyloxylation step taking place in the presence of an alkali metal carbonate and dimethylformamide solvent and intermediates therefor.

More specifically, our invention defines a process which is commercially useful for producing triconjugated dienones defined according to the structure:

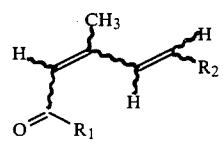

including tagetones defined according to the structure:

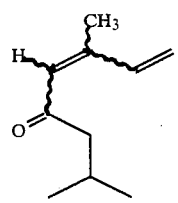

as well as the compounds having the structures:

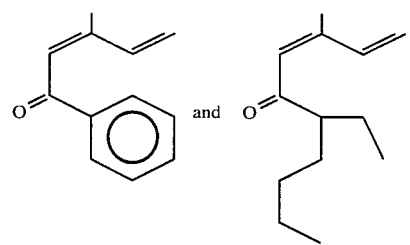

In summary, the process of our invention is illustrated according to the following reaction sequence:

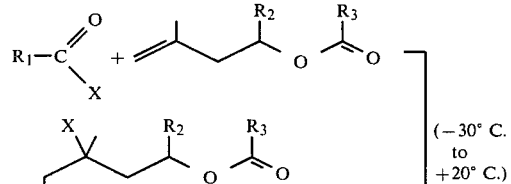

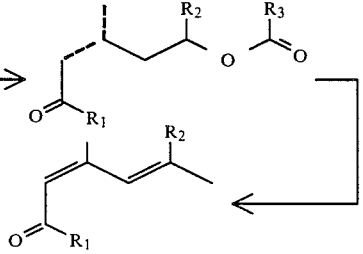

wherein $R_3$ is represents $C_1$–$C_5$ alkyl.

This process is carried out by first reacting an acyl halide defined according to the structure:

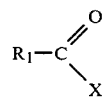

(where X represents chloro)
with an ester defined according to the structure:

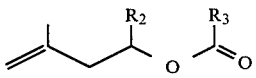

in the presence of an aluminum chloride catalyst and a methylene dichloride solvent. The mole ratio of the aluminum trichloride: the ester defined according to the structure:

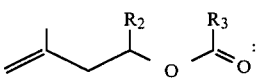

the acyl halide should be about 2:1:1. Excess of any of the constituents does not give rise to any more efficient or faster reaction and does give rise to a problem concerning elimination of unreacted reactants. The reaction temperature should be in the range of from about −30° C. up to about +20° C., preferably from about −20° C. up to about 0° C. The ability to carry out the reaction in this temperature range creates an unexpected great advantage over any similar reactions known in the prior art which similar reactions must be carried out at about −78° C.

In this first reaction the compound defined according to the structure:

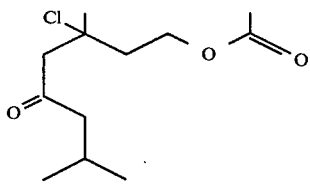

is formed.

The intermediate having the structure:

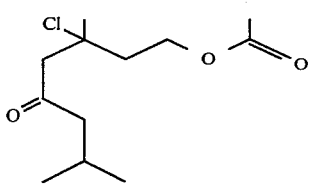

is a novel compound.

The compounds defined according to the structure:

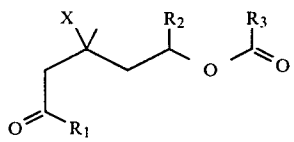

are then dehydrohalogenated using as a dehydrohalogenating agent an alkali metal carbonate in the presence of a dimethylformamide solvent. Examples of alkali metal carbonates are sodium carbonate, potassium carbonate and lithium carbonate. This part of our process proceeds in two steps: (1) the first step to form the compound having the structure:

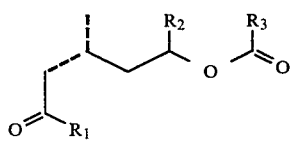

wherein one of the dashed lines is a carbon-carbon double bond and the other of the dashed lines is a carbon-carbon single bond; and (2) then continuing the reaction as a dehydroacyloxylation reaction to form the triconjugated dienone compounds defined according to the structure:

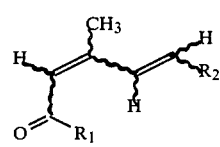

including that defined according to the structure:

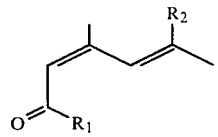

The temperature of the first step of the reaction may vary between about 80° C. and 100° C. The temperature for the second step may vary between about 100° C. and about 150° C. and most conveniently, the temperature for the second step is from 105° C. up to 110° C. at atmospheric pressure. For both steps the pressure is preferably atmospheric but may be super atmospheric (1–10 atmospheres) and less than atmospheric (0.5 atmospheres up to 1 atmosphere).

The mole ratio of alkali metal carbonate:haloester defined according to the structure:

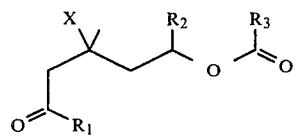

may vary from about 2:1 down to about 1:1 with a preferred mole ratio of between about 1:1 and about 1.5:1. The concentration of the haloester reactant in the dimethylformamide solvent may vary from about 0.1 moles per liter up to about 1.5 moles per liter with a mole ratio of about 0.4 moles per liter being preferred.

The triconjugated dienones of our invention can be used to contribute powerful floral, tagete-like aromas to perfumes, perfumed articles and colognes. Examples of perfumed articles are anionic, cationic, nonionic or zwitterionic detergents, perfumed polymers, fabric softener compositions and dryer-added fabric softeners. As olfactory agents the triconjugated dienones of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones other than the triconjugated dienones of our invention, nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundationstone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the triconjugated dienones of this invention which will be effective in perfume compositions depends on many factors, including the other ingredients, their amounts and the effects which are desired. It has been found that perfume compositions containing as little as 0.1% of the triconjugated dienones of this invention, or even less, can be used to impart an interesting floral tagete-like aroma to soaps, liquid and solid cationic, anionic, nonionic or zwitterionic detergents, cosmetics, powders, liquid and solid fabric softeners, optical brightener compositions, perfumed polymers and other products. The amount employed can range up to 50% or higher and will depend on considerations of cost, nature of the end product, and the effect desired on the finished product and particular fragrance sought.

The triconjugated dienones of this invention including the compounds having the structures:

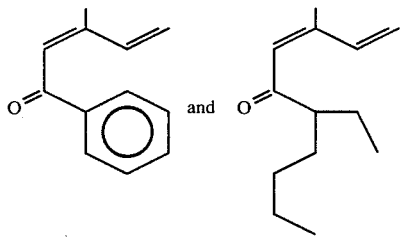

can be used alone or in a perfume composition as an olfactory component in detergents and soaps, space odorants and deodorants; colognes, toilet waters; bath salts; hair preparations such as lacquers, brilliantines, pomades, and shampoos; cosmetic preparations such as creams, deodorants, hand lotions and sun screens; powders such as talcs, dusting powders, face powder, and the like. When used as an olfactory component of a perfumed article, as little as 0.01% of one or more of the triconjugated dienones will suffice to impart an interesting tagete-like, floral aroma. Generally, no more than 0.5% based the perfumed article is required.

In addition, the perfume composition can contain a vehicle or carrier for the triconjugated dienones alone or with other ingredients. The vehicle can be a liquid such as an alcohol such as ethanol, a glycol such as propylene glycol, or the like. The carrier can be an absorbent solid such as a gum or components for encapsulating the composition such as gelatin which can be used to form a capsule wall surrounding the perfume oil as by means of coacervation.

An additional aspect of our invention provides an organoleptically improved smoking tobacco product and additives therefor including methods of making the same which overcome problems heretofore encountered in the creation or enhancement of specific desired sweet, fruity and green notes with tagete nuances. Such notes, both prior to and on smoking, in both the main stream and the side stream, may now be readily controlled and maintained at the the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby sweet, fruity, green and tagete-like notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the triconjugated dienones of our invention.

In addition to the triconjugated dienones of our invention, other flavoring and aroma additives may be added to the smoking tobacco material or substitute therefor either separately or in mixture with one or more of the triconjugated dienones of our invention as follows:

I. SYNTHETIC MATERIALS

Beta-methylcinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl-5-isopropylacetophenone;
2-Hydroxy-2,5,5,8a(-tetramethyl-1-)2-hydroxyethyl)-decahydronaphthalene;
Dodecahydro-3a,6,6,9a-tetramethylnaphtho(2,1-B)-furan;
4-Hydroxyhexenoic acid, gamma-lactone;
Polyisoprenoid hydrocarbons defined in Example V of U.S. Pat. No. 3,589,372 issued on June 29, 1971

II. NATURAL OILS

Celery seed oil;
Coffee extract;
Bergamot oil;
Cocoa extract;
Nutmeg oil;
Origanum oil;

An aroma and flavoring concentrate containing one or more of the triconjugated dienones of our invention and if, if desired, one or more of the above-indicated additional flavoring additives may be added to the smoking tobacco material, to the filter or to the leaf or paper wrapper or to a filter which is part of the smoking article. The smoking tobacco material may be shredded, cured, cased on blended tobacco material or reconstituted tobacco material or tobacco substitutes (e.g., lettuce leaves) or mixtures thereof. The proportions of flavoring additives may be varied in accordance with taste, but insofar as enhancement or the imparting of sweet, fruity, green and tagete-like notes prior to and on smoking, in both the main stream and the side stream, we have found that satisfactory results are obtained if the proportion by weight of the sum total of the triconjugated dienones to smoking tobacco material is between 50 ppm and 1500 ppm (0.005%–0.15%) of the active ingredients to the smoking tobacco material. We have further found that satisfactory results are obtained if the proportions by weight of the sum total of the triconjugated dienones used to flavoring material is between 0.05:1 and 0.50:1.

Any convenient method for incorporating the triconjugated dienones of our invention in the tobacco products may be employed. Thus the triconjugated dienones taken alone or along with other flavoring additives may be dissolved in a suitable solvent such as food grade ethanol, pentane, diethyl ether and/or other volatile organic solvents, and the resulting solution may either be sprayed on the cured, cased and blended tobacco material; or the tobacco material or filter may be dipped into such solution. Under certain circumstances, a solution of one or more of the triconjugated dienones of our invention taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have one or more of the triconjugated dienones of our invention in excess of the amounts of concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated supra, the triconjugated dienones of our invention can be incorporated with materials such as filter tip materials, seam paste, packaging materials and the like which are used along with the tobacco to form a product adapted for smoking. Furthermore, the triconjugated dienones of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts of substitute materials or both.

It will thus be apparent that the triconjugated dienones of our invention can be utilized to alter, modify, augment or enhance sensory properties, particularly organoleptic properties, such as flavor(s) and/or fragrance(s) of a wide variety of consumable materials.

The following examples are illustrative of our invention and the invention is not to be limited thereto but is only intended to be limited by the claims.

EXAMPLE I

PREPARATION OF METHYL BUTENOL ACETATE

Reaction:

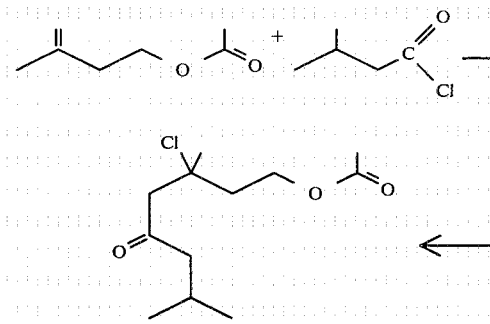

Into a 2-liter 3 neck flask equipped with stirrer, thermometer, reflux condenser and 1-liter addition funnel with nitrogen blanket apparatus and cool water bath is placed 1.5 grams of paratoluene sulphonic acid (0.00789 moles) and 587 grams (5.75 moles) of acetic anhydride. The resulting mixture is stirred at room temperature (20°–30° C.).

Over a period of one hour while maintaining the reaction mass at 60° C. to 70° C., from the addition funnel 472 grams (1.00 moles) of 3-methyl-3-buten-1-ol is added to the reaction mass with stirring. The reaction mass is maintained at 63° C. to 64° C. for 0.5 hours, after which time, 0.65 grams (0.00789 moles) of anhydrous sodium acetate is added to the reaction mass.

The reaction mass is then distilled and the distillate is added to a mixture of 1400 ml ice and water. The oil phase is then extracted from the resulting mixture using one 500 ml portion of methylene chloride followed by one 200 ml portion of methylene dichloride. The resulting extract is then washed as follows:

1–250 ml portion of 4% sodium bicarbonate
1–100 ml saturated sodium bicarbonate
1–250 ml portion of water The reaction product is then dried over anhydrous sodium sulfate and filtered. The resulting filtrate is then distilled on a 2″ splash column at 55° C. to 78° C. vapor temperature and 63° C. to 140° C. liquid temperature at 55 mm/Hg pressure. The resulting material is redistilled at 57° C. to 67° C. vapor temperature at 55 mm/Hg pressure yielding 1043 grams of product.

EXAMPLE II

FORMATION OF HALO ESTER INTERMEDIATE AND TAGETONE

Reactions:

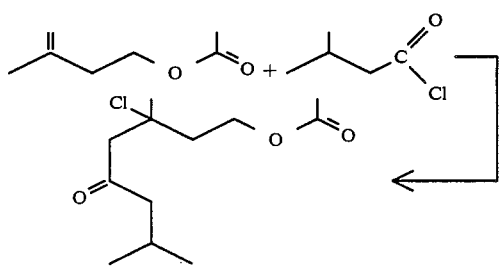

-continued

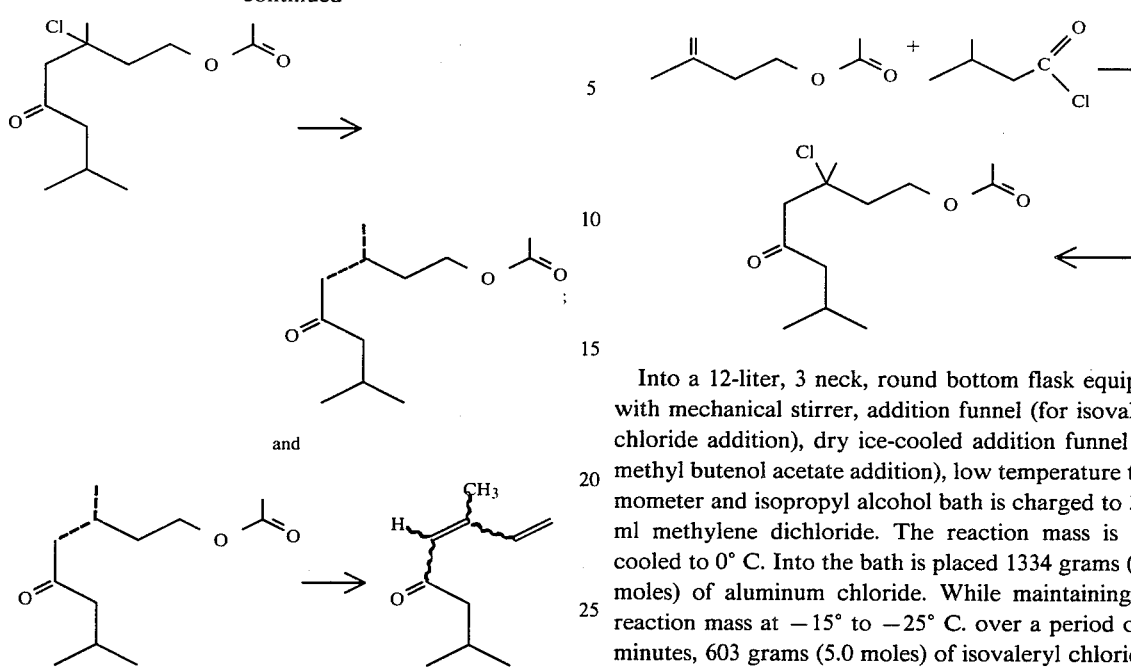

Into a 25 ml of 3 neck round bottom flask equipped with magnetic stirrer, thermometer, reflux condenser and nitrogen inlet tube is placed 1.0 grams (0.0078 moles) of aluminum trichloride; 5 ml methylene dichloride; and 1 gram (0.0078 moles) of isovaleryl chloride. The reaction mass is cooled to 0° C. and via a pipette over a period of one minute while maintaining the reaction temperature at 0° to 8° C., 1 gram of 3-methyl-3-butenol acetate (0.0078 moles) produced according to Example I is added to the reaction mass. The reaction mass is stirred for a period of 10 minutes at 0° C. to 4° C.

5 Ml methylene dichloride is then added to the reaction mass. The reaction mass is stirred for a period of 0.5 hours at a temperature of 0° C. to 20° C.

FIG. 1 is the NMR spectrum for the tagetone product contained in the reaction product defined according to the structure:

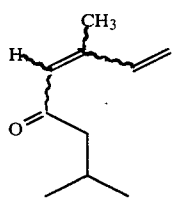

wherein the wavy lines represents a "cis" and "trans" juxtaposition of the vinyl and methyl and acyl moieties about the carbon-carbon double bond which is alpha to the acyl moiety. The ratio of "cis" to "trans" isomer is 10:4. (Solvent: CFCl$_3$; field strength 100 MHz).

EXAMPLE III

PREPARATION OF HALO ACETATE INTERMEDIATE

Reaction:

Into a 12-liter, 3 neck, round bottom flask equipped with mechanical stirrer, addition funnel (for isovaleryl chloride addition), dry ice-cooled addition funnel (for methyl butenol acetate addition), low temperature thermometer and isopropyl alcohol bath is charged to 3000 ml methylene dichloride. The reaction mass is then cooled to 0° C. Into the bath is placed 1334 grams (10.0 moles) of aluminum chloride. While maintaining the reaction mass at $-15°$ to $-25°$ C. over a period of 15 minutes, 603 grams (5.0 moles) of isovaleryl chloride is added to the reaction mass.

While maintaining the reaction mass at $-15°$ to $-40°$ C. over a period of 1 hour, 640 grams (5.0 moles) of 3-methyl-3-butenol acetate is added to the reaction mass. The reaction mass is then stirred for a period of 0.5 hours while maintaining the temperature at $-15°$ to $-40°$ C.

The reaction mass is then added to 7500 grams of ice in a 22-liter separatory funnel. 5000 Ml water is then added and the organic phase is separated from the aqueous phase. The organic phase is washed as follows:

(a) one-5000 ml portion of water
(b) one-3500 ml portion of 7% sodium bicarbonate (pH=8)

The reaction mass is dried over anhydrous sodium sulfate and 1.2 grams Ionol ® and 1.2 grams of butylated hydroxy anisole is added to the reaction mass. The reaction mass is then filtered and the filtrate is used in Example IV.

The filtrate consists of the compound defined according to the structure:

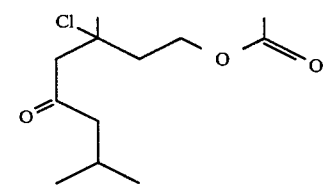

as confirmed by GLC, NMR and IR mass spectral analyses.

FIG. 2 is the GLC profile for the product. The peaks indicated by reference numeral "22A", "22B" and "22C" are the peaks for the chloro acetate compound having the structure:

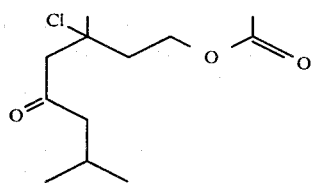

EXAMPLE IV

PREPARATION OF TAGETONE

Reactions:

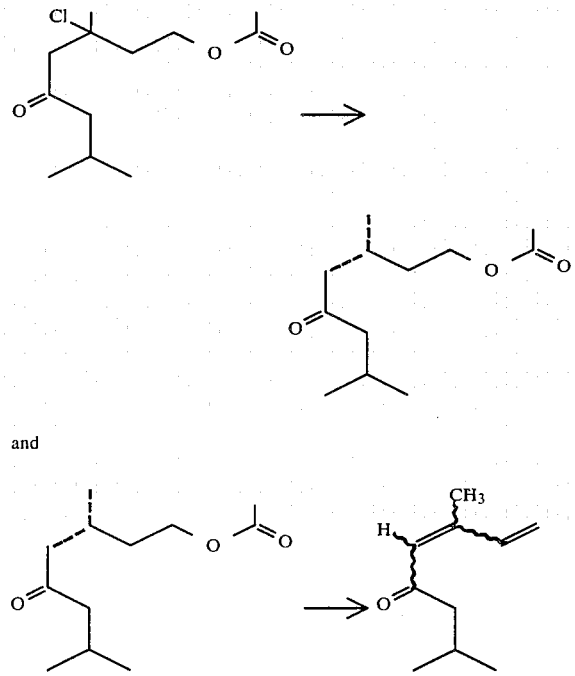

and (wherein the dashed lines in the molecules showing dashed lines represent mixtures of molecules wherein in the mixtures in each of the molecules one of the dashed lines is a carbon-carbon double bond and the other of the dashed lines is a carbon-carbon single bond; and wherein in the molecules showing wavy lines, the wavy lines represent the "cis" and "trans" juxtaposition of the methyl, vinyl and acyl moieties about the carbon-carbon double bond which is alpha to the acyl moiety).

Into a 12-liter, 3 neck flask equipped with mechanical stirrer, 6" splash column, packed with large saddles, reflux head, adapter, 2-liter Erlenmeyer flask (as receiver) wide tube, thermometer with nitrogen inlet, heating mantle, 1-liter addition funnel with vacuum adapter is placed 2500 ml of dimethylformamide and 915 grams (8.63 moles) sodium carbonate. The resulting mixture is stirred and heated to 80° C.

While maintaining the reaction mass at 80° to 96° C., 4-liters of a solution containing 1243 grams (5.00 moles) of the halo acetate having the structure:

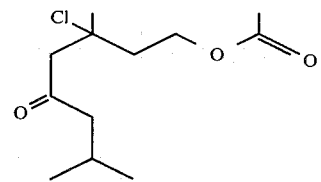

prepared according to Example III is added to the reaction mass over a period of 2.0 hours. During the addition methylenedichloride is distilled from the reaction product. After completion of the addition of the methylene chloride/chloro acetate reactant solution, the reaction mass is continued to be distilled at a pot temperature of 100° to 110° C. and a vapor temperature of 70° to 80° C. for a period of 1 hour. (1400 Ml of methylenedichloride is distilled). The reaction mass is then continued to be heated at a temperature of 105° to 111° C. and a pressure of 4-50 mm/Hg. The reaction mass is then cooled to 15° C. and 8000 ml of water and ice mixture is added to the reaction mass.

The reaction mass is then transferred to a 22-liter separatory funnel using an additional 6-liters of water. 850 Ml methylenedichloride is added to the reaction mass. The organic phase is separated from the aqueous phase and the aqueous phase is extracted with 850 ml methylene dichloride and the methylene dichloride extract is added to the organic phase.

The organic phase is then washed as follows:
1. 2500 ml portion of water
2. 1–3000 ml portion of water
3. 1–3000 ml portion of water
4. 1–3000 ml portion of water The reaction mass is then dried over anhydrous sodium sulphate and 0.76 grams of butylated hydroxy anisole is added. The reaction mass is then evaporated on a rotary evaporator at 15 to 20 mm/Hg pressure and 30° to 35° C. The crude product (weight: 758 grams) is then stripped of solvent and distilled on a 3" splash column yielding the following fractions:

| Fraction No. | Vapor Temp. (°C.) | Liquid Temp. (°C.) | Vacuum mm/Hg. Pressure |
|---|---|---|---|
| 1 | 45/57 | 71/73 | 1.45/1.65 |
| 2 | 63 | 76 | 1.75 |
| 3 | 60 | 76 | 1.5 |
| 4 | 65 | 88 | 1.2 |
| 5 | 70 | 105 | 1.2 |
| 6 | 68 | 123 | 1.0 |
| 7 | 80 | 151 | 1.0 |

Fractions 2 and 3 are then bulked and redistilled on a 1.5"×24" vacuum jacketed column packed with ¾" saddles to yield the following fractions:

| Fraction No. | Vapor Temp. (°C.) | Liquid Temp. (°C.) | Vacuum mm/Hg. Pressure | % Tagetones | Weight of Fraction |
|---|---|---|---|---|---|
| 1 | 43/48 | 69/68 | 1.8/1.8 | 54.6 | 10.5 |
| 2 | 50.0 | 67.5 | 1.8 | 60.2 | 7.6 |
| 3 | 52.5 | 68.5 | 1.8 | 67.4 | 10.6 |
| 4 | 54.5 | 69.0 | 1.9 | 74.5 | 11.0 |
| 5 | 55.0 | 69.5 | 1.9 | 80.1 | 16.3 |
| 6 | 55.5 | 70.0 | 1.9 | 82.3 | 15.3 |
| 7 | 55.5 | 70.0 | 1.9 | 85.0 | 14.4 |
| 8 | 56.0 | 70.5 | 1.9 | 88.2 | 20.6 |

-continued

| Fraction No. | Vapor Temp. (°C.) | Liquid Temp. (°C.) | Vacuum mm/Hg. Pressure | % Tagetones | Weight of Fraction |
|---|---|---|---|---|---|
| 9 | 56.0 | 71.5 | 1.9 | 91.2 | 19.1 |
| 10 | 56.5 | 72.5 | 1.9 | 91.4 | 16.7 |
| 11 | 57.0 | 73.0 | 1.9 | 94.9 | 37.5 |
| 12 | 57.0 | 73.0 | 1.9 | 96.0 | 40.2 |
| 13 | 57.5 | 74.0 | 1.9 | 97.1 | 39.6 |
| 14 | 57.5 | 78.0 | 1.9 | 97.4 | 40.8 |
| 15 | 57.5 | 91.0 | 1.9 | 97.6 | 28.1 |
| 16 | 52.0 | 120.0 | 0.9 | 97.7 | 12.2 |
| 17 | 40.0 | 14.0 | 0.4 | 95.1 | 2.5 |
| 18 | 35/62 | 158/175 | 0.4 | 72.8 | 2.3 |

FIG. 3 is the GLC profile for Example IV.

EXAMPLE V

Reaction:

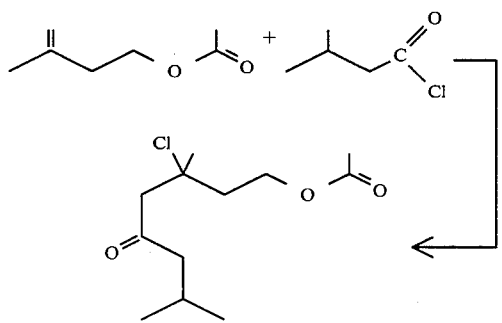

Into a 1000 ml, 4 neck round bottom flask equipped with mechanical stirrer, thermometer, glass wool outlet, addition funnels with nitrogen inlet, heating mantle and dry ice/isopropyl alcohol bath is placed 192 ml of methylene dichloride. The reaction mass is cooled to −20° C. and 95 grams (0.50 ml) of titanium tetrachloride is charged to the reaction mass.

Over a period of 5 minutes while maintaining the reaction temperature of −20° to −25° C., 30.2 grams (0.25 moles) of isovaleryl chloride is added to the reaction mass.

While maintaining the reaction temperature −17° to −24° C. over a period of 20 minutes, 32 grams (0.25 moles) of 3-methyl-3-butenol acetate prepared according to Example I is added to the reaction mass.

The reaction mass is then stirred at −17° to −24° C. for a period of 1 hour.

The reaction mass is then added to 800 ml of an ice-/water mixture. The reaction mass is then transferred to a 2-liter separatory funnel and the organic layer is separated from the aqueous phase. The organic phase is washed with one 300 ml portion of water followed by 300 ml saturated sodium bicarbonate. The reaction mass is then dried over over anhydrous sodium sulfate and filtered. The filtrate contains a substantial amount of chloro acetate having the structure:

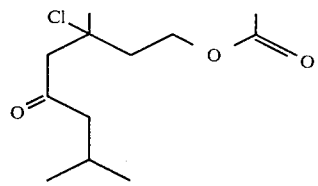

as well as impurities.

FIG. 4 is the GLC profile for the reaction product. The peaks indicated by reference numeral "42A", "42B" and "42C" are for the compound having the structure:

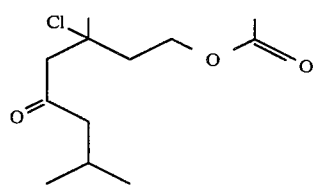

The peak indicated by reference numeral "41" is the peak for the substantial impurity in the reaction product.

EXAMPLE VI(A)

Reaction:

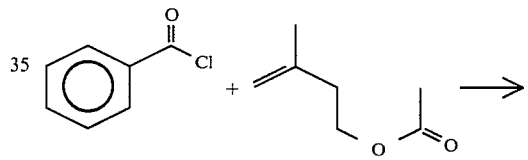

Into a 100 ml, 3 neck, round bottom flask equipped with magnetic stirrer, low temperature thermometer, addition funnel, with nitrogen inlet, adapter, and dry ice bath is placed 29 ml of methylene dichloride and 9.18 grams (0.0690 moles) of aluminum chloride. The resulting mixture is cooled to −10° to −25° C. and over a period of 20 minutes, 4.84 grams (4 ml) (0.0345 moles) of benzoyl chloride is added to the reaction mass with stirring.

While maintaining the reaction mass at a temperature of between −15° and −40° C. over a period of 20 minutes, 4.4 grams (0.0345 moles) of 3-methyl-3-butenol acetate is added to the reaction mass. The reaction mass is stirred at −15° to −30° C. over a period of 1 hour.

The reaction mass is then poured into 5 grams of ice with stirring. The organic phase is separated from the aqueous phase. The organic phase is washed with one 50 ml portion of water followed by two 50 ml portions of saturated sodium bicarbonate. The resulting product is dried and concentrated to yield a compound having the structure:

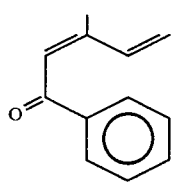

EXAMPLE VI(B)

Reaction:

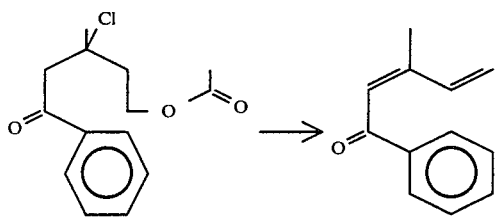

Into a 100 ml, 3 neck flask, equipped with magnetic stirrer, 50 ml addition funnel, with nitrogen inlets, thermometer, distillation column with reflux head and heating mantle is placed 6.3 grams (0.0595 moles) of sodium carbonate and 20 ml of dimethylformamide. The reaction mass is heated to 85° C. and over a period of six minutes, 9.3 grams (0.0345 moles) of the compound having the structure:

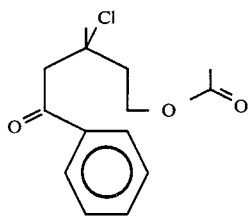

is added to the reaction mass. The reaction mass is then stirred at a pot temperature of 88°–110° C. and a vapor temperature of 48°–63° C. for a period of two hours. At the end of the two hour period the reaction mass is poured into 200 ml cold water and the oil phase separates from the aqueous phase. The aqueous phase is washed with two 25 ml portions of methylene dichloride and the methylene dichloride extract is combined with the organic phase. The organic phase is then washed with four 50 ml portions of water and dried over anhydrous sodium sulfate.

FIG. 5 is the GLC profile for the reaction mass. The peak indicated by reference numeral "51" is the peak for the compound having the structure:

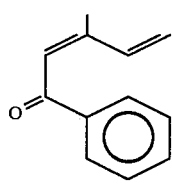

FIG. 6 is the NMR spectrum for the compound having the structure:

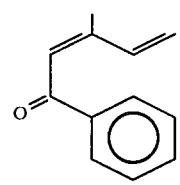

(solvent: $CFCl_3$; field strength 100 MHz).

FIG. 7 is the infra-red spectrum for the compound having the structure:

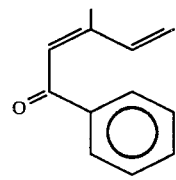

The resulting product having the structure:

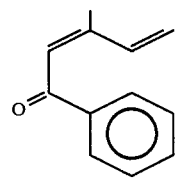

has an interesting tagete/floral aroma profile.

EXAMPLE VII(A)

Reaction:

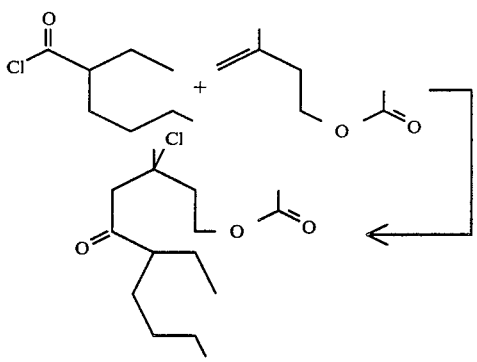

Into a 500 ml, 4 neck flask, equipped with mechanical stirrer, low temperature thermometer, adapter and addition funnels and dry ice isopropyl alcohol bath is placed a mixture of 46.3 grams (0.348 moles) of aluminum chloride and 168 ml methylene dichloride. The reaction mass is cooled to a temperature of −13° C. and over a period of three minutes, 28.2 grams (0.174 moles) of 2-ethyl-hexanoyl chloride is added to the reaction mass. While maintaining the reaction mass temperature at −15° to −17° C. over a period of twenty-five minutes, 22.2 grams (0.174 moles) of 3-methyl-3-butenol acetate is added to the reaction mass with stirring. The reaction mass is continued to be stirred for a period of 20 minutes. At the end of this period of time, the reaction mass is poured into 500 ml ice with stirring. The organic phase separates from the aqueous phase. The aqueous phase is extracted with 50 ml of methylene dichloride extract and the organic phase are combined and washed as follows:
one-300 ml portion of water;
one-200 ml portion of saturated sodium bicarbonate;
one-100 ml portion of water.

The reaction product is dried over anhydrous sodium sulfate. The reaction product has the structure:

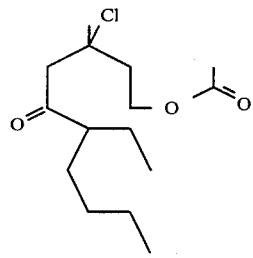

EXAMPLE VII(B)

Reaction:

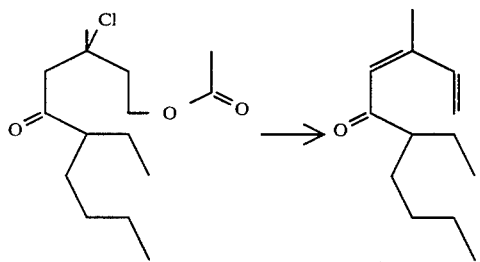

Into a 500 ml, 4 neck flask, equipped with thermometer, mechanical stirrer, vigreux column, claissen distillation head with Friedrichs condenser, 500 ml addition funnel and 1-liter Erlenmeyer flask as receiver is placed one hundred 2 ml dimethylformamide and 31.8 grams (0.300 moles) of sodium carbonate. The reaction mass is heated to 85° C. and over a period of twenty minutes 50.6 grams (0.174 moles) of the compound having the structure:

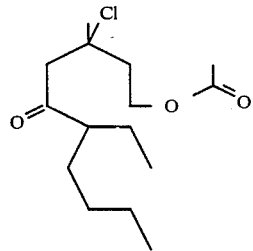

is added to the reaction mass with stirring. The reaction mass is then heated at a pot temperature of 105°–110° C. and a vapor temperature of 63°–64° C. for a period of 2.1 hours. At the end of the 2.1 hour period, the reaction mass is cooled and the reaction mixture is poured into 600 ml cold water. The aqueous phase separates from the organic phase and the organic phase is extracted with two 130 ml portions of methylene dichloride. The extracts are combined and washed with 300 ml water. The resulting product is dried over anhydrous sodium sulfate.

FIG. 8 is the GLC profile of the reaction product. The peak indicated by reference numeral "81" is the peak for the product having the structure:

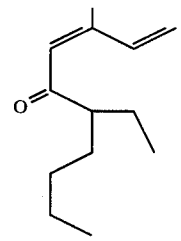

FIG. 9 is the NMR spectrum for the compound having the structure:

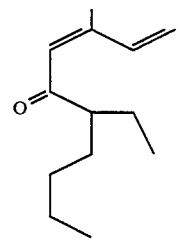

(Solvent: CFCl₃; field strength MHz).

FIG. 10 is the infra-red spectrum for the compound having the structure:

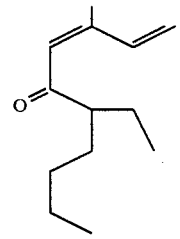

EXAMPLE VIII

The following basic jasmine formulations are prepared:

| Ingredients | Parts by Weight | |
|---|---|---|
| | VIII(A) | VIII(B) |
| Benzyl Acetate | 30.0 | 30.0 |
| Phenyl Ethyl Alcohol | 20.0 | 20.0 |
| Eugenol | 0.2 | 0.2 |
| Geraniol | 2.0 | 2.0 |
| Benzyl Alcohol | 20.2 | 20.2 |
| Linalool | 5.0 | 5.0 |
| Indole-10% in Diethyl phthalate | 0.5 | 0.5 |
| Ylang Ylang Oil | 0.1 | 0.1 |
| Isophytol | 10.0 | 10.0 |
| Jasmine Absolute | 1.0 | 1.0 |
| Amyl Cinnamic Aldehyde | 5.0 | 5.0 |
| Benzyl Propionate | 5.0 | 5.0 |
| Compound having the structure: | 1.0 | — |

| Ingredients | Parts by Weight | |
|---|---|---|
| | VIII(A) | VIII(B) |
| 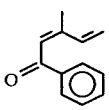 | | |
| Compound having the structure: 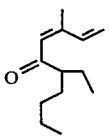 | — | 1.0 |

An intense tagete/floral aroma which fits well into the jasmine topnote is produced using either the compound having the structure:

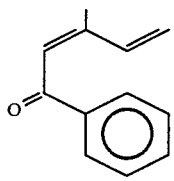

produced according to Example VI or the compound having the structure:

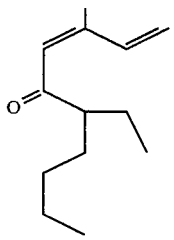

produced according to Example VII. These compounds make the jasmine aroma much longer lasting and add the interesting tagete/floral nuance making it much more natural-like.

EXAMPLE IX

PREPARATION OF A COSMETIC POWDER COMPOSITION

A cosmetic power is prepared by mixing in a ball mill, 100 grams of talcium powder with 0.25 grams of composition of matter as set forth in the table below. Each of the cosmetic powders prepared with each of the ingredients of the composition of matters set forth in Table II below has an aroma as set forth in Table II below:

TABLE II

| Perfumery Substanve | Aroma |
|---|---|
| Compound having the structure: | A tagete/floral aroma. |

TABLE II-continued

| Perfumery Substanve | Aroma |
|---|---|
| 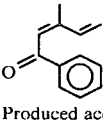 Produced according to Example VI. | |
| Compound having the structure: 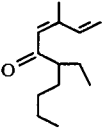 Produced according to Example VII. | A tagete/floral aroma. |
| Perfume composition of Example VIII(A). | A jasmine aroma with tagete and floral nuances. |
| Perfume composition prepared according to Example VIII(B). | A jasmine aroma with tagete and floral nuances. |

EXAMPLE X

PERFUMED LIQUID DETERGENT

Concentrated liquid detergents (Lysine salt of n-dodecylbenzene sulfonic acid, as more specifically described in U.S. Pat. No. 3,948,818 issued on Apr. 6, 1976) (the specification for which is incorporated by reference herein) with aroma nuances as set forth in Table II of Example IX, supra, are prepared containing 0.10%, 0.15% and 0.20% of the fragrance set forth in Table II of Example IX, supra. They are prepared by adding and homogeneously mixing the appropriate quantity of fragrance formulation as set forth in Table II of Example IX in the liquid detergent. The detergents all possess excellent aromas as set forth in Table II of Example IX, the intensity increasing with greater concentrations of perfume composition of Table II of Example IX.

EXAMPLE XI

PREPARATION OF COLOGNES AND HANDKERCHIEF PERFUMES

Compositions as set forth in Table II of Example IX are incorporated into colognes at concentrations of 2.0%, 2.5%, 3.0%, 3.5%, 4.0%, 4.5% and 5.0% in 85%, 90% and 95% aqueous food grade ethanol solutions, and into handkerchief perfumes at concentrations of 15%, 20%, 25% and 30% (in 85%, 90% and 95% aqueous food grade ethanol solutions). Distinctive and definitive aromas as set forth in Table II of Example IX are imparted to the cologne and to the handkerchief perfume at all levels indicated above.

EXAMPLE XII

PREPARATION OF SOAP COMPOSITION

One hundred grams of soap chips (IVORY ®, registered trademark of the Procter and Gamble Co. of Cinncinati, Ohio) are mixed with one gram of each of the perfume substantives of Table II of Example IX until a homogeneous composition is obtained. The homogeneous composition is then treated under three atmospheres pressure at 180° C. for a period of three hours and the resulting liquid is placed in soap molds. The resulting soap cake, on cooling, manifests an excellent aromas as set forth in Table II of Example IX.

EXAMPLE XIII

PREPARATION OF A SOLID DETERGENT COMPOSITION

A detergent is prepared from the following ingredients according to Example I of Canadian Pat. No. 1,007,948 (the specification of which is incorporated by reference herein):

| Ingredients | Percent by Weight |
|---|---|
| "Neodol 45-II" (a $C_{14}$-$C_{15}$) alcohol ethoxylated with 11 moles of ethylene oxide | 12 |
| Sodium carbonate | 55 |
| Sodium citrate | 20 |
| Sodium sulfate, water brighteners q.s. | |

The detergent is a "phosphate-free" detergent. A total of 100 grams of this detergent is admixed with 0.15 grams of each of the perfume substantives of Table II of Example IX. The detergent samples each have aromas as set forth in Table II of Example IX.

EXAMPLE XIV

Utilizing the procedure of Example I of column 15 of U.S. Pat. No. 3,632,396 (the specification for which is incorporated by reference herein), a nonwoven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of each of the perfume substances of Table II of Example IX A fabric softening composition prepared as set forth above having the above aroma characteristics, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aromas set forth in Table II of Example IX are imparted in a pleasant manner to the head space in the dryer on operation thereof, using said dryer-added fabric softening non-woven fabric.

The disclosure of U.S. Pat. No. 3,632,396 in its entirety is hereby incorporated into the instant patent application. Thus, the fabric softening articles as covered by U.S. Pat. No. 3,632,396 can all be incorporated with the perfume composition of Table II of Example IX.

EXAMPLE XV

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes:

| Ingredient | Parts by Weight |
|---|---|
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with the mixture compound produced according to Example VI having the structure:

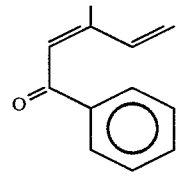

at 100 ppm per cigarette. Another one-third of these model cigarettes are treated in the filter with the compound having the structure:

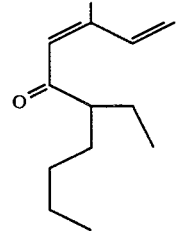

produced according to Example VII at the rate of $2 \times 10^{-5}$ grams per gram of filter. When evaluated by paired comparison, the cigarettes treated both in the tobacco and in the filter with the compositions, respectively, of Example VI and VII are found in smoke flavor to be more tobacco-like with sweet, fruity, green, tagete-like aromas prior to and on smoking in the main stream and in the side stream.

What is claimed is:

1. A process for preparing a triconjugated dienone defined according to the structure:

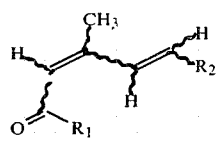

wherein $R_1$ is $C_1$–$C_8$ alkyl, phenyl or phenyl methyl and $R_2$ is hydrogen or $C_1$–$C_5$ alkyl; and wherein the wavy lines represent the "cis" and "trans" juxtaposition of the vinyl, methyl, acyl and $R_2$ moieties about one or both of the carbon-carbon double bonds comprising the steps of:

(i) reacting an acyl halide having the structure:

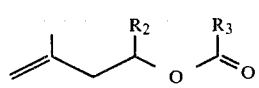

wherein X represents chloro with an ester having the structure:

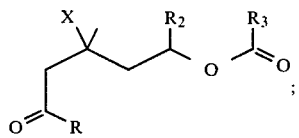

in the presence of an aluminum chloride catalyst and a methylene dichloride solvent in order to form the compound having the structure:

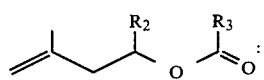

wherein $R_3$ is $C_1$–$C_5$ alkyl, the mole ratio of aluminum trichloride:ester defined according to the structure:

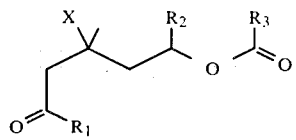

acyl halide being about 2:1:1, the reaction temperature being in the range of from about −30° C. up to about +20° C.; then (ii) dehydrohalogenating the compound having the structure:

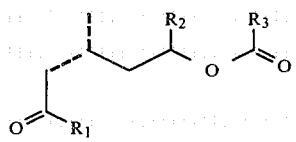

with a dehydrohalogenation agent comprising an alkali metal carbonate and dimethylformamide to form a compound defined according to the structure:

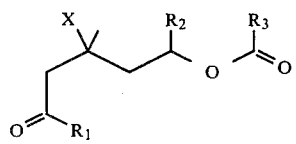

wherein one of the dashed lines is a carbon-carbon double bond and the other of the dashed lines is a carbon-carbon single bond; and wherein X represents chloro, bromo or iodo, the temperature of reaction being between about 80° C. and 100° C., the mole ratio of alkali metal carbonate:haloester defined according to the structure:

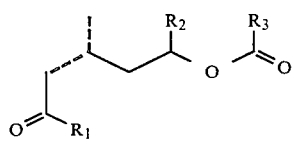

being from about 2:1 down to about 1:1; the concentration of the haloester reactant in the dimethylformamide solvent varying from about 0.1 moles per liter up to about 1.5 moles per liter; and then (iii) dehydroacyloxylating the resulting compound having the structure:

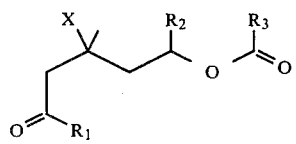

with an alkali metal carbonate and dimethylformamide at a temperature of from about 100° C. up to about 150° C. thereby forming the compound having the structure:

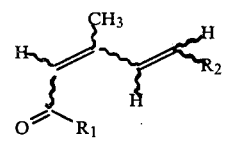

2. The process of claim 1 wherein $R_1$ is 2-methyl-1-propyl; X is chloro; $R_2$ is hydrogen; and $R_3$ is methyl.

* * * * *